(12) United States Patent
Gastner et al.

(10) Patent No.: US 8,703,819 B2
(45) Date of Patent: Apr. 22, 2014

(54) USE OF GUANIDINOACETIC ACID (SALTS) COMBINATION WITH BETAINE AND/OR CHOLINE TO PRODUCED AN AGENT THAT IS BENEFICIAL TO HEALTH

(75) Inventors: Thomas Gastner, Engelsberg (DE); Hans-Peter Krimmer, Kirchweidach (DE)

(73) Assignee: Alzchem Trostberg GmbH, Trostberg (DE)

( * ) Notice: Subject to any disclaimer, the term of this patent is extended or adjusted under 35 U.S.C. 154(b) by 649 days.

(21) Appl. No.: 12/525,103

(22) PCT Filed: Jan. 23, 2008

(86) PCT No.: PCT/EP2008/000501
§ 371 (c)(1),
(2), (4) Date: Jul. 30, 2009

(87) PCT Pub. No.: WO2008/092591
PCT Pub. Date: Aug. 7, 2008

(65) Prior Publication Data
US 2010/0055182 A1  Mar. 4, 2010

(30) Foreign Application Priority Data
Jan. 31, 2007  (DE) .......................... 10 2007 004 781

(51) Int. Cl.
*A61K 31/195* (2006.01)
*A61K 31/205* (2006.01)
*A61K 31/14* (2006.01)

(52) U.S. Cl.
USPC ............................ 514/565; 514/556; 514/642

(58) Field of Classification Search
None
See application file for complete search history.

(56) References Cited

U.S. PATENT DOCUMENTS

| 2,761,807 | A | 9/1956 | Borsook et al. |
| 5,998,457 | A | 12/1999 | Kaddurah-Daouk |
| 6,927,231 | B2 | 8/2005 | Droge |
| 2005/0085543 | A1 | 4/2005 | Wallimann et al. |
| 2005/0287204 | A1 * | 12/2005 | Hageman et al. ............. 424/451 |
| 2008/0161387 | A1 | 7/2008 | Gastner et al. |

FOREIGN PATENT DOCUMENTS

| DE | 2 441 777 A1 | 3/1976 |
| DE | 10 2005 009990 A1 | 9/2006 |
| DE | 695 35 104 T2 | 2/2007 |
| DE | 10 2006 035 801 A1 | 4/2007 |
| JP | 1056614 A | 3/1989 |
| WO | WO 9107954 * | 6/1991 |
| WO | WO93/03714 | 3/1993 |
| WO | WO97/13507 | 4/1997 |
| WO | WO01/00203 A1 | 1/2001 |
| WO | WO 01/54676 A2 | 8/2001 |
| WO | WO 2004/000042 A | 12/2003 |
| WO | WO2004000297 | 12/2003 |
| WO | WO 2004/071406 A | 8/2004 |
| WO | WO2005120246 | 12/2005 |
| WO | WO 2005120246 A1 * | 12/2005 |

OTHER PUBLICATIONS

Fatterpaker et al. Influence of folic acid and vitamin B12 on formation of creatine in vitro and in vivo. Nature (1951) 167; 1067-1068.*
Wyss et al. Creatine and Creatinine Metabolism. Physiological Reviews (Jul. 2000) vol. 80, No. 3, pp. 1107-1213.*
Craig, Betaine in Human Nutrition, Am J. Clin. Nutr. 2004:80-539-49.
Borsook, et al. "The Biochemical Basis of Betaine-Glycocyamine Therapy", *Annals of West. Med. and Surgery*, vol. 5, No. 10 (1951), pp. 825-829.

* cited by examiner

*Primary Examiner* — Daniel Sullivan
*Assistant Examiner* — Peter Anthopolos
(74) *Attorney, Agent, or Firm* — Fulbright & Jaworski LLP

(57) ABSTRACT

The use of guanidinoacetic acid and/or salts thereof in combination with choline and/or betaine to produce an agent for improving brain function, bone growth and the mineralization of bones, for improving cartilage growth, for alleviating aging processes, for strengthening the immune system, as an antioxidative and neuroprotective agent, for lowering the cholesterol and triglyceride value, for preventing inflammatory processes and for lowering the blood sugar level in humans and vertebrates is described.
In this connection it has surprisingly turned out that the new agents have a considerably higher bioavailability and are thus better taken up into the cells than was previously known when using creatine.

24 Claims, 1 Drawing Sheet

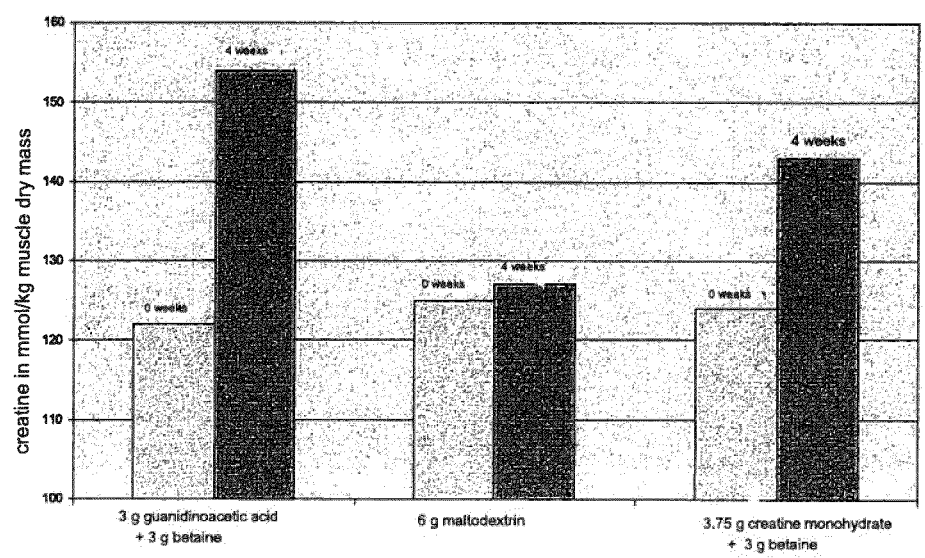

USE OF GUANIDINOACETIC ACID (SALTS) COMBINATION WITH BETAINE AND/OR CHOLINE TO PRODUCED AN AGENT THAT IS BENEFICIAL TO HEALTH

RELATED APPLICATIONS

This application is a §371 application from PCT/EP2008/000501 filed Jan. 23, 2008 which claims priority from Germany Patent Application No. 10 2007 004 781.0 filed Jan. 31, 2007, each of which is herein incorporated by reference in its entirety.

DESCRIPTION

The present invention concerns the use of guanidinoacetic acid or salts thereof to produce an agent that is beneficial to health.

Guanidinoacetic acid was isolated for the first time in the year 1934 by C. J. Weber from the urine of dogs and humans. Weber already assumed that it is a metabolic precursor of creatine (Weber, C. J., Proc. Sot. Exp. Biol. and Med., 33, 172 (1934)).

A little later it was shown that guanidinoacetic acid is in fact an endogenous substance which occurs in animals as well as in humans and which plays a central role in the biosynthesis of creatine. Creatine can be assimilated from food and it can also be formed endogenously. The biosynthesis starts from glycine and L-arginine. In mammals the guanidino group of L-arginine is cleaved and an N-C-N group is transferred onto glycine by the enzyme aminotransferase especially in the kidneys, but also in the liver and the pancreas. In this process L-arginine is converted into L-ornithine. The guanidinoacetic acid formed in this manner is converted in the next step into creatine with the aid of the enzyme transmethylase which in vertebrates takes place exclusively in the liver. In this step S-adenosylmethionine serves as a methyl group donor. The creatine is subsequently transported via the blood circulation to the target organs. In this connection transport through the cell membrane into the cells occurs by means of a specific NaCl-dependent creatine transporter (Speer O., Neukomm L. J., Murphy R. M, Zanolla E., Schlattner U., Henry H., Snow R. J., Wallimann T. Creatine transporters: a reappraisal. Mol. Cell Biochem. 2004 January-February 256-257 (1-2): 407-24).

Creatine plays an important role in the energy metabolism of the cell where in the form of energy-rich phosphocreatine it is an important energy reserve of the muscle in addition to adenosine triphosphate (ATP). In the resting state of the muscle ATP can transfer a phosphate group onto creatine to form phosphocreatine which is then in a direct equilibrium with ATP. During muscle work it is of crucial importance that the ATP stores are filed up again as rapidly as possible. Phosphocreatine is available for this purpose in the first seconds of maximum muscle load. Phosphocreatine can transfer a phosphate group onto adenosine diphosphate in a very rapid reaction by the enzyme creatine kinase and thus re-form ATP. This is also referred to as the Lohmann reaction.

Furthermore, creatine has an important function in the transfer of energy in the cell. The so-called creatine shuttle system transports energy from the mitochondria to the sites in the cell at which energy is required.

During intense and prolonged muscle work the creatine stores that are naturally present in the body are rapidly exhausted. For this reason selective doses of creatine have a positive effect on endurance and performance especially in the case of competitive athletes and undesired accumulation processes in the body or disadvantageous degradation products are unknown. The reason for this is that creatine is excreted by the body via the kidneys when there is an excess supply. Furthermore, creatine is converted at a constant rate into the cyclic degradation product creatinine which is also excreted via the kidneys and thus represents a second metabolic degradation path.

The ergogenic effect of creatine has been systematically investigated since the end of the 70s of the past century. More than 300 studies have been carried out in the sport field to date and about 80% of these studies showed significant positive effects of creatine on muscle mass, muscular strength, the fat-free body mass and the performance at maximum, short-term muscular exertion in various sports.

Creatine monohydrate is nowadays the most important food supplement in the field of sports.

Only recently have further interesting properties of creatine become known. Thus, in two studies an oral creatine supplementation was proven to have significant positive effects on brain performance and the ability to concentrate (Rae, Caroline et al.: Oral creatine monohydrate supplementation improves brain performance: a double-blind, placebo-controlled, cross-over trial. Proceedings of the Royal Society of London, Series B: Biological Sciences (2003), 270(1529), 2147-2150; Watanabe, Airi et al.: Effects of creatine on mental fatigue and cerebral hemoglobin oxygenation. Neuroscience Research (Oxford, United Kingdom) (2002), 42(4), 279-285.

Furthermore, it was shown that creatine has antioxidative and neuroprotective properties and can thus also be used to prevent damage to cells caused by environmental influences (Sestili, Piero et al.: Creatine supplementation affords cytoprotection in oxidatively injured cultured mammalian cells via direct antioxidant activity. Free Radical Biology & Medicine (2006), 40(5), 837-849; P. Klivenyi et al.: Neuroprotective effects of creatine in a transgenic animal model of amnyotrophic lateral sclerosis. Nature Medicine 5, 347-350 (1999)).

The ratio of cysteine to cystine in plasma can be used as a simple to measure indicator for oxidative stress in the human body (Hack et al.: BLOOD 92 (1998) 59-67). In this connection the ratio of these components directly reflects the redox state where oxidative stress is characterized by an increase in the cystine value. It is known that oxidative stress in the human body can be prevented by a creatine supplementation. The cystine values could also be considerably lowered even in older test persons by a supplementation with a few grams creatine per day and led to values like those found in healthy young people (U.S. Pat. No. 6,927,231). Creatine considerably reduces oxidative stress and thus has a preventive effect on degenerative aging processes. Creatine and derivatives thereof will therefore in future also become much more important in the anti-aging field.

The positive effects of creatine are currently being intensively investigated also in the medical field where creatine is in the clinical phase 3 for the treatment of Parkinson and amyotrophic lateral sclerosis (ALS) and in phase 2 for Huntington's chorea (EP 804 183 B1). A successful use of creatine as a therapeutic agent for asthma has also already been reported (EP 911 026 B1). Creatine exhibited positive effects in vitro as well as in vivo in the formation of bone. The use for strengthening bones and for treating and preventing degenerative bone and cartilage diseases such as osteoporosis has been investigated and yielded very positive results (EP 1 100 488 B1; Gerber, I et al.: Stimulatory effects of creatine on metabolic activity, differentiation and mineralization of primary osteoblast-like cells in monolayer and micromass cell cultures. European Cells and Materials (2005), 10, 8-22; Chilibeck, P. D. et al.: Creatine monohydrate and resistance training increase bone mineral content and density in older men. Journal of Nutrition, Health & Aging (2005), 9(5), 352-355).

Furthermore, it is known that a creatine supplementation leads to an increase in body mass. This is initially due to an increased uptake of water into muscles. However, in the long term creatine indirectly results in an increased protein synthesis or a reduced protein catabolism in the myofibrils leading to an increase in muscle mass (Int. J. Sports Med. 21 (2000), 139-145). Hence, as a result the fat-free body mass is increased.

In addition to creatine itself i.e. the creatine monohydrate, numerous creatine salts have also meanwhile proven to be suitable food supplements such as creatine ascorbate, citrate, pyruvate and others. The European patent EP 894 083 and the German laid-open patent specification DE 197 07 694 A1 are mentioned here as representative prior art.

Several working groups already showed in clinical studies in the fifties of the last century that the administration of guanidinoacetic acid in combination with betaine has a positive effect on the course of the disease in heart diseases. The patients reported a considerable improvement of their general condition. Furthermore, an improved endurance during physical exertion and an increased muscle power was already found after a short treatment period. The patients also reported an improved libido. 200 Patients were administered a dose of 30 mg/kg daily for one year. Side-effects were not observed (Borsook H.: Borsook M. E.: The biochemical basis of betaine-glycocyamine therapy. In: Annals of western medicine and surgery 5(10), 825, 1951).

The International patent application WO 91/07 954 discloses the use of guanidinoacetic acid in combination with methionine or S-adenosylmethionine to increase the creatine level in muscle. Conditions which require an increased creatine level in muscle are mentioned as the field of application. Medical applications as well as the field of sport nutrition are claimed in this connection.

It is claimed that creatine is ineffective for increasing the creatine level. This assertion has meanwhile been disproven by numerous publications (e.g. Persky, A. M., Brazeau, G. A.: Clinical Pharmacology of the Dietary Supplement Creatine Monohydrate. In: Pharmacol Rev. 2001, 53, 161-176).

The International patent application WO 2004/000 297 describes a mixture for dietary or pharmaceutical purposes which is used for mammals. This composition consists of a protein fraction containing L-serine and guanidinoacetic acid as an additional component. In this connection the mixture must be free of glycine or after hydrolysis the mixture must contain a ratio of L-serine to glycine of more than 2.7 to 1. Solutions, emulsions, suspensions, gels, bars, sweets and preferably powders are specified as possible product forms.

This ratio of L-serine to glycine of more than 2.7 to 1 is not normally found in foods and animal feed. Animal raw materials such as e.g. animal meal contain considerably more glycine than serine (Amino acids of meals of animal origin. de Vuyst, A. Univ. Louvain, Belgium, Agricultura (Heverlee, Belgium) (1964), 12(1), 141-51). In plant raw materials the ratio between glycine and serine is mainly balanced.

The uptake of creatine into the musculature is controlled by an NaCl-dependent creatine transporter and can be positively influenced by the simultaneous uptake of a large amount of carbohydrates or proteins. In this connection it has been shown that a combination of creatine and carbohydrates can lead to a 60% higher increase in the creatine contents in muscles compared to the sole ingestion of creatine (Green A L, Hultman E, Macdonald I A, Sewell D A, Greenhaff P L. Carbohydrate ingestion augments skeletal muscle creatine accumulation during creatine supplementation in humans. Am. J. Physiol. 1996 Nov. 271 (5 Pt 1); E821-6).

In addition to its undisputed positive physiological properties creatine, however, also has the disadvantage that it does not have a pronounced stability in the corresponding aqueous solutions. In this connection creatine cyclizes due to the cleavage of water to form creatinine. The rate of cyclization depends on the pH of the solution and on the temperature where the concentration does not play a role. The conversion into creatinine proceeds very rapidly especially in a neutral and acidic pH range. The rapid degradation of creatine in this environment practically excludes its use in aqueous or moist formulations for human and animal nutrition. The pH of the stomach of 1 to 2 can already lead to a considerable degradation of creatine to creatinine depending of the retention time (Greenhaff, P. L.: Factors Modifying Creatine Accumulation in Human Skeletal Muscle. In: Creatine. From Basic Science to Clinical Application. Medical Science Symposia Series Volume 14, 2000, 75-82).

The described disadvantages of the prior art have resulted in the object of the present invention of providing an agent that is beneficial to health which supplies the body cells more efficiently with creatine and thus achieves to an even higher degree the known positive physiological effects of a supplementation with creatine in the human and animal body. The negative properties of creatine such as its low stability in aqueous and acidic environments should be avoided. In this connection above all the low stability of creatine in food preparations with a high water content should also be mentioned which considerably limits the possible applications of creatine in industrially produced foods. Furthermore, the instability after uptake in the stomach poses a major problem. Hence, the aim was to supply the body more efficiently with creatine than can occur when creatine is directly administered.

In order to optimally increase the creatine contents in body cells, it was previously necessary to simultaneously ingest a large amount of carbohydrates or proteins. This should also be avoided as far as possible because it results in the secretion of large amounts of insulin which in the long term can lead to health problems.

This object was achieved by the use of guanidinoacetic acid and salts thereof in combination with choline and/or betaine to produce an agent for improving brain function, bone growth and the mineralization of bones, for improving the growth of cartilage, for alleviating aging processes, as an antioxidative and neuroprotective agent, for lowering the cholesterol and triglyceride value, for preventing inflammatory processes and for lowering the blood sugar level in humans or vertebrates.

It was possible to show that the object of optimally supplying the body cells with creatine could be completely fulfilled by using guanidinoacetic acid in combination with choline and/or betaine. In this connection the known positive effects of creatine in humans and vertebrates were achieved with an even higher effectiveness. Surprisingly it has turned out that the new agents have a considerably higher bioavailability and are thus taken up into the cells better than was previously known when using creatine.

In contrast to creatine or creatine monohydrate, guanidinoacetic acid and salts thereof have a considerably higher stability even in an acidic solution such as that which occurs in the stomach. Surprisingly it has turned out to be particularly advantageous that the guanidinoacetic acid and salts thereof described in the present connection are thus, in contrast to creatine, not in fact converted into creatine mainly in the liver until after resorption. Thus, in contrast to the known creatine, the compounds used are for the most part not already previously degraded by instability reactions and excreted, but are in fact available for the physiological fields of application. Thus, according to the invention guanidinoacetic acid and salts thereof in combination with choline and/or betaine result in considerably higher creatine contents in the target organs again in contrast to creatine and derivatives thereof. A simultaneous ingestion of large amounts of sugars or proteins is no longer necessary due to the present invention and is a major advantage from a nutritional physiological perspective since it avoids the secretion of unphysiological amounts of insulin.

Furthermore, it was possible to show that guanidinoacetic acid and salts thereof in combination with choline and/or betaine have a very high stability under conditions such as those which occur during the industrial production of foods and animal feeds and in addition are more stable when stored in practically any form of administration. In this connection guanidinoacetic acid in combination with choline and/or betaine exhibits clear advantages over creatine. The advantages of the use claimed by the invention were thus not forseeable in their entirety.

The fields of application in humans and vertebrates that are claimed by the present invention are the use of guanidinoacetic acid in combination with choline and/or betaine to improve brain function by oral supplementation with guanidinoacetic acid and salts thereof in combination with choline and/or betaine. In this case long-term memory as well as short-term memory were positively influenced. Furthermore, the test persons were able to concentrate for a considerably longer time.

Bone growth and the mineralization of bones as well as cartilage growth was also improved by guanidinoacetic acid and salts thereof in combination with choline and/or betaine. In this connection it turned out that the agent according to the invention leads to an even better deposition of calcium in the bones compared to creatine. Furthermore, antioxidative and neuroprotective effects were observed.

Guanidinoacetic acid in combination with choline and/or betaine is also suitable for alleviating aging processes where it had a positive effect on the muscle mass, the amount of tissue water, the calcium values in the cell and cell aging.

Another field of application of guanidinoacetic acid in combination with choline and/or betaine is the prevention of inflammatory processes and fortification of the immune system. In one experiment rats were fed guanidinoacetic acid and choline chloride, creatine monohydrate or a placebo and after 6 weeks they were exposed to a bacterial infection (Staphylococcus aureus). The supplementation with guanidinoacetic acid and choline chloride resulted in a considerably higher survival rate compared to the creatine group and also to the control group. Furthermore, the infection triggered considerably milder inflammatory processes in the guanidinoacetic acid group. It was also possible to verify this effect by measuring the CRP protein in the serum of the rats.

Guanidinoacetic acid and salts thereof in combination with choline and/or betaine is also excellently suitable for lowering the cholesterol and triglyceride values as well as for lowering the blood sugar level where the observed effects in all cases exceeded the effect of creatine.

Of the guanidinoacetic acid salts which come into consideration for the intended use according to the invention, in particular salts have proven to be advantageous that are obtained with aspartic acid, ascorbic acid, pyruvic acid, succinic acid, fumaric acid, gluconic acid, α-ketoglutaric acid, oxalic acid, pyroglutamic acid, 3-nicotinic acid, lactic acid, citric acid, maleic acid, sulphuric acid, acetic acid, formic acid, hydrochloric acid and phosphoric acid, 2-hydroxybenzoic acid, L-carnitine, acetyl L-carnitine, taurine, betaine, choline, methionine and lipoic acid, where potassium, calcium or sodium guanidinoacetate are particularly suitable. Of course mixtures of guanidinoacetic acid with one or more of the above-mentioned salts or mixtures of the above-mentioned salts can be used.

According to a preferred embodiment the agent according to the invention is used in combination with additional methyl group donors selected from the group dimethylglycine, sarcosine, folic acid and methionine or a mixture of these components.

A further advantage of the use according to the invention has turned out to be the fact that guanidinoacetic acid and salts thereof can be used in a relatively wide dosage range. In this connection the single doses as well as the daily doses are not subject to any restrictions. Preferably single doses of 0.001 to 0.3 g/kg come into consideration with regard to the use as a food supplement, medical preparation, functional food and animal feed where single doses of 0.05 to 0.15 g/kg are regarded as particularly preferred.

The methyl group donors choline and betaine can also be used in a relatively wide dosage range. Preferably single doses of 0.001 to 0.4 g/kg choline and betaine come into consideration with regard to the use as a food supplement, medical preparation, functional food and animal feed where single doses of 0.03 to 0.25 g/kg are regarded as particularly preferred.

The molar ratio of the amount used of guanidinoacetic acid to choline and/or betaine should be in a range of 1:5 to 5:1, were a ratio of 1:3 to 2:1 and in particular of 1:1 is regarded as particularly preferred.

It is important for the invention that the claimed use of guanidinoacetic acid and salts thereof in combination with choline and/or betaine is carried out for humans or vertebrates, preferably pets, breeding animals and animals for fattening. The following come primarily into consideration as dosage forms: powders, granulates, lozenges, capsules, pellets, solutions, juices or jelly products.

Another field of application envisaged by the present invention is the use as an animal feed where in particular dry feed, semi-moist feed and wet feed in the form of canned feed, pellets, biscuits, croquettes, nuggets, flakes and snacks are suitable.

The guanidinoacetic acid and/or salts thereof in combination with choline and/or betaine are used in the form of an edible matrix as a further aspect of the present invention. In this case it is particularly advantageous when the guanidinoacetic acid or salts thereof are present in the respective edible matrix as crystalline solids or solids in powder form. In this connection it is regarded as preferred when a separation of the components is delayed or preferably prevented by the physical properties of the edible matrix. These preferred properties of the edible matrix can be assisted by adding viscosity-increasing substances such as alginates, xanthan, guar flour or locust bean flour. Thus solid, semi-liquid and liquid foods are suitable as edible matrices. In order to improve the taste it may be advantageous to mill guanidinoacetic acid or salts thereof for this intended use. The substance to be incorporated is preferably homogeneously distributed in the edible matrix which can be carried out manually (e.g. by the end user) and/or mechanically. Dairy products such as yoghurt, whey, cheese and milk are mentioned here as examples. In addition guanidinoacetic acid is suitable for incorporation into industrially manufactured finished products and semi-finished products such as noodles, muesli, cereals, bakery products, ready meals, bars, bread, sausage and drinks in which the guanidinoacetic acid (salts) has (have) been incorporated during the production process. In this connection it has surprisingly turned out that the stability of the guanidinoacetic acid or salts thereof can be further increased by this incorporation and the pH of the edible matrix does not have a significant effect on the stability. Thus, practically all foods can be used in the manner according to the invention where a pH of the matrix between 2 and 11 is particularly suitable. Furthermore, the proposed food products are a very convenient and practical form for the daily ingestion of guanidinoacetic acid and salts thereof in combination with choline and/or betaine.

The formulations according to the invention still contain at least 90% of the originally used guanidinoacetic acid and/or salts thereof after 90 days storage at room temperature. In most matrices the amount that is still present after 90 days is more than 95% and in particular more than 99%. This high stability has previously not been achieved for creatine under comparable conditions and reference is made in particular to the document EP 1180944.

Choline as well as betaine are incorporated simultaneously with guanidinoacetic acid into the edible matrices in a preferred embodiment and are completely stable under the manufacturing conditions as well as under the storage conditions of the edible matrices.

Depending on the respective specific application it may indeed be advisable to use the agent proposed according to the invention in combination with other physiologically active nutrients from the group comprising carbohydrates, fats, amino acids, proteins, vitamins, mineral substances, trace elements, caffeine, taurine and derivatives and mixtures thereof.

Overall the present invention with the new fields of application for guanidinoacetic acid in combination with choline and/or betaine offers much more than only new alternatives to the known creatine compounds since the composition according to the invention overcomes the disadvantages of creatine and represents a very considerable improvement due to its better bioavailability and higher effectiveness.

The broadness of the present invention is illustrated by the following examples.

EXAMPLES

Example 1

Food Supplements and Medical Preparations

Typical compositions of delicious formulations are listed in the following the components of which have been dry-mixed at room temperature. It is recommended to dissolve the formulations in powder form in 200 ml fruit juice and/or water before oral ingestion.

| 1.1 | 1500 mg | glucosamine |
|---|---|---|
|  | 750 mg | guanidinoacetic acid |
|  | 720 mg | magnesium-L-hydrogen aspartate |
|  | 500 mg | ascorbic acid |
|  | 720 mg | choline citrate |
| 1.2 | 400 mg | chondroitin sulfate |
|  | 500 mg | guanidinoacetic acid pyruvate |
|  | 2000 mg | dicalcium phosphate |
|  | 400 mg | $(MgCO_3)_4 Mg(OH)_2 \cdot 5H2O$ =! about 100 Mg |
|  | 500 mg | vitamin C |
|  | 800 mg | betaine |
| 1.3 | 1000 mg | glucosamine |
|  | 300 mg | choline chloride |
|  | 2800 mg | guanidinoacetic acid |
|  | 3100 mg | creatinol-O-phosphate |

Example 2

Feed Additive 2.1 A formulation consisting of 5000 mg guanidinoacetic acid, 3000 mg choline chloride and 5000 mg inulin was introduced into a typical formulation for feed pellets in order to supplement dog food.

2.2 A formulation consisting of 7000 mg guanidinoacetic acid lipoate, 5000 mg choline chloride, 750 mg carnitine tartrate, 100 mg sucrose stearate, 160 mg talcum and 1090 mg fructose was introduced into the base composition for dog biscuits.

2.3 The following formulation was homogeneously introduced into a commercial canned cat food mixture as a master batch: 3000 mg guanidinoacetic acid pyruvate, 4000 mg choline chloride, 3000 mg creatine, 40 mg magnesium stearate, 25 mg carboxymethylcellulose and 135 mg lactose.

Example 3

Functional Foods 3.1 A mixture of 5 kg guanidinoacetic acid and 8 kg choline chloride is homogeneously incorporated into 900 kg of a bread baking mixture.

3.2 A mixture of 5 kg betaine and 7 kg guanidinoacetic acid lipoate is homogeneously incorporated into a spread cheese preparation.

3.3 20 kg betaine, 10 g folic acid and 14 kg guanidinoacetic acid were homogeneously incorporated into a fruit preparation for a yoghurt before the sterilization.

3.4 3 g guanidinoacetic acid and 3 g betaine were homogeneously introduced into a muesli bar.

3.5 Cornflakes were manufactured from a mixture of maize, malt extract, salt, 30 kg guanidinoacetic acid and 40 kg choline bitartrate.

Example 4

Biological Availability and Action 4.1 Four groups of test subjects of in each case 20 persons were assembled such that approximately the same average initial value of creatine was present in the muscle dry mass in all groups.

Over four weeks one group was administered daily an inventive functional food (muesli bar) according to example 3.4. which contained 3 g guanidinoacetic acid and 3 g betaine (group 1). The second group received a muesli bar containing 6 g maltodextrin (group 2) and the third group received a muesli bar which contained 3.75 g creatine monohydrate (equimolar to 3 g guanidinoacetic acid) and 3 g betaine (group 3). The fourth group received a muesli bar containing 3 g guanidinoacetic acid (group 4). The creatine contents in the muscle were measured by means of a muscle biopsy immediately before the study and after four weeks of ingestion. The results are shown in FIG. 1.

A 60 minute standardized fitness programme was carried out with all test subjects during the four weeks. The physical and mental performance as well as a series of 5 blood parameters were measured before and after the four week ingestion. The results are summarized in table 1.

TABLE 1

|  | cholesterol value | triglyceride value | BDS (1) | RAPM (2) | bone density | cystine value | blood sugar level |
| --- | --- | --- | --- | --- | --- | --- | --- |
| group 1 | −8% | −26% | 2.7 | 5.7 | 4% | −24% | −8% |
| group 2 | 1% | −3% | 0.8 | 1.5 | 0% | −3% | 2% |
| group 3 | −5% | −21% | 2.1 | 4.4 | 2.50% | −15% | −5% |
| group 4 | −4% | −22% | 2.3 | 4.6 | 2.80% | −14% | −5% |

Table 1 shows the difference between the respective initial measurement and the measurement after the four week supplementation.
(1) BDS (backward digit span): A sequence of numbers was read to the test subjects who had to repeat the sequence backwards. The number of correctly repeated numbers before the supplementation was subtracted from the number of correctly repeated numbers after the supplementation.
(2) RAPM (Raven's Advanced Progressive Matrices): A standardized intelligence test was carried out with the test subjects. The score achieved before supplementation was subtracted from the score after the supplementation.
4.2 Three groups of F344 rats (Charles River Wiga GmbH, Sulzfeld) each of 25 animals were fed for six weeks with a standard feed to which (group 1) guanidinoacetic acid (0.5%) and choline chloride (0.5%), (group 2) creatine monohydrate (0.63%) and choline chloride (0.5%) and (group 3) maltodextrin (1%) were added.

After the six weeks all animals were intravenously injected with 1.0 ml of a Staphylococcus aureus suspension ($3 \times 10^6$ bacteria per ml). The survival rate and the CRP serum level of the surviving animals was assessed after three days (table 2).

TABLE 2

|  | Survival rate | CRP serum level |
| --- | --- | --- |
| group 1 | 80% | 3.4 mg/dl |
| group 2 | 68% | 4.5 mg/dl |
| group 3 | 48% | 7.3 mg/dl |

(CRP = C-reactive protein)

The invention claimed is:
1. A method comprising:
   administering guanidinoacetic acid or a salt thereof (GAA) and the methyl group donors choline and betaine (MGDCB) at a molar ratio in the range of from 1 GAA:1 MGDCB to 2 GAA:1 MGDCB, where MGDCB corresponds to moles of choline plus moles of betaine, to a human to improve bone growth, to mineralize bones, to grow cartilage, to alleviate an aging process, to have an antioxidative and neuroprotective effect, to lower cholesterol and triglyceride values, to prevent an inflammatory process, or to lower a blood sugar level.
2. The method of claim 1, wherein the molar ratio is 2 GAA:1 MGDCB.

3. The method of claim 1, wherein (1) the GAA is in the form of a powder, granulate, lozenge, capsule, pellet, solution, juice or jelly product; (2) the choline is in the form of a powder, granulate, lozenge, capsule, pellet, solution, juice or jelly product; and (3) the betaine is in the form of a powder, granulate, lozenge, capsule, pellet, solution, juice or jelly product.

4. The method of claim 1, wherein the GAA, the choline, and the betaine are administered in the form of an edible matrix comprising GAA, choline, and betaine.

5. The method of claim 4, wherein the edible matrix is in the form of a beverage, solid food product, or semi-solid food product.

6. The method of claim 4, wherein the edible matrix further comprises a physiologically-active substance selected from the group consisting of carbohydrate, fat, amino acid, protein, vitamin, mineral, trace element, caffeine, taurine, and combinations thereof.

7. The method of claim 1, wherein the guanidinoacetic acid is in the form of a salt comprising a substance selected from the group consisting of malic acid, aspartic acid, ascorbic acid, succinic acid, pyruvic acid, fumaric acid, gluconic acid, α-ketoglutaric acid, oxalic acid, pyroglutamic acid, 3-nicotinic acid, lactic acid, citric acid, sulphuric acid, acetic acid, formic acid, hydrochloric acid, phosphoric acid, 2-hydroxybenzoic acid, L-carnitine, acetyl-L-carnitine, lipoic acid, sodium, potassium, and calcium.

8. The method of claim 1, wherein the guanidinoacetic acid or a salt thereof is administered in a single dose of 0.001 to 0.3 g/kg body weight of the human.

9. A method comprising:
   administering guanidinoacetic acid or a salt thereof (GAA) and choline at a molar ratio in the range of from 1 GAA:1 choline to 2 GAA:1 choline to a human, to improve bone growth, to mineralize bones, to grow cartilage, to alleviate an aging process, to have an antioxidative and neuroprotective effect, to lower cholesterol and triglyceride values, to prevent an inflammatory process, or to lower a blood sugar level; and
   wherein no betaine is co-administered to the human.

10. The method of claim 9, wherein the molar ratio is 2 GAA:1 choline.

11. The method of claim 9, wherein (1; ) the GAA is in the form of a powder, granulate, lozenge, capsule, pellet, solution, juice or jelly product; and (2) the choline is in the form of a powder, granulate, lozenge, capsule, pellet, solution, juice or jelly product.

12. The method of claim 9, wherein the GAA and the choline are administered in the form of an edible matrix comprising GAA and choline.

13. The method of claim 12, wherein the edible matrix is in the form of a beverage, solid food product, or semi-solid food product.

14. The method of claim 12, wherein the edible matrix further comprises a physiologically-active substance selected from the group consisting of carbohydrate, fat, amino acid, protein, vitamin, mineral, trace element, caffeine, taurine, and combinations thereof.

15. The method of claim 9, wherein the guanidinoacetic acid is in the form of a salt comprising a substance selected from the group consisting of malic acid, aspartic acid, ascorbic acid, succinic acid, pyruvic acid, fumaric acid, gluconic acid, α-ketoglutaric acid, oxalic acid, pyroglutamic acid, 3-nicotinic acid, lactic acid, citric acid, sulphuric acid, acetic acid, formic acid, hydrochloric acid, phosphoric acid, 2-hydroxybenzoic acid, L-carnitine, acetyl-L-carnitine, lipoic acid, sodium, potassium, and calcium.

16. The method of claim 9, wherein the guanidinoacetic acid or a salt thereof is administered in a single dose of 0.001 to 0.3 g/kg body weight of the human.

17. A method comprising:
   administering guanidinoacetic acid or a salt thereof (GAA) and betaine at a molar ratio in the range of from 1 GAA:1 betaine to 2 GAA:1 betaine to a human, to improve bone growth, to mineralize bones, to grow cartilage, to alleviate an aging process, to have an antioxidative and neuroprotective effect, to lower cholesterol and triglyceride values, to prevent an inflammatory process, or to lower a blood sugar level; and
   wherein no choline is co-administered to the human.

18. The method of claim 17, wherein the molar ratio is 2 GAA:1 betaine.

19. The method of claim 17, wherein (1) the GAA is in the form of a powder, granulate, lozenge, capsule, pellet, solution, juice or jelly product; and (2) the betaine is in the form of a powder, granulate, lozenge, capsule, pellet, solution, juice or jelly product.

20. The method of claim 17, wherein the GAA and the betaine are administered in the form of an edible matrix comprising GAA and betaine.

21. The method of claim 20, wherein the edible matrix is in the form of a beverage, solid food product, or semi-solid food product.

22. The method of claim 20, wherein the edible matrix further comprises a physiologically-active substance selected from the group consisting of carbohydrate, fat, amino acid, protein, vitamin, mineral, trace element, caffeine, taurine, and combinations thereof.

23. The method of claim 17, wherein the guanidinoacetic acid is in the form of a salt comprising a substance selected from the group consisting of malic acid, aspartic acid, ascorbic acid, succinic acid, pyruvic acid, fumaric acid, gluconic acid, α-ketoglutaric acid, oxalic acid, pyroglutamic acid, 3-nicotinic acid, lactic acid, citric acid, sulphuric acid, acetic acid, formic acid, hydrochloric acid, phosphoric acid, 2-hydroxybenzoic acid, L-carnitine, acetyl-L-carnitine, lipoic acid, sodium, potassium, and calcium.

24. The method of claim 17, wherein the guanidinoacetic acid or a salt thereof is administered in a single dose of 0.001 to 0.3 g/kg body weight of the human.

* * * * *

UNITED STATES PATENT AND TRADEMARK OFFICE
CERTIFICATE OF CORRECTION

PATENT NO. : 8,703,819 B2
APPLICATION NO. : 12/525103
DATED : April 22, 2014
INVENTOR(S) : Thomas Gastner et al.

It is certified that error appears in the above-identified patent and that said Letters Patent is hereby corrected as shown below:

On the Title Page, Item (54) and in the Specification, Column 1, Lines 1-4, replace the title with the following:

-- USE OF GUANIDINOACETIC ACID (SALTS) IN COMBINATION WITH BETAINE AND/OR CHOLINE TO PRODUCE AN AGENT THAT IS BENEFICIAL TO HEALTH --.

Signed and Sealed this
Eighth Day of July, 2014

Michelle K. Lee
*Deputy Director of the United States Patent and Trademark Office*